United States Patent [19]

Kurandt

[11] Patent Number: 4,838,697

[45] Date of Patent: Jun. 13, 1989

[54] APPARATUS FOR RAPID COLORIMETRY ON DIFFERENT SAMPLES

[76] Inventor: Fritz Kurandt, Blankenhainer Strasse 21, D-1000 Berlin 46, Fed. Rep. of Germany

[21] Appl. No.: 81,905

[22] Filed: Aug. 5, 1987

[30] Foreign Application Priority Data

Aug. 5, 1986 [DE] Fed. Rep. of Germany ....... 3626373

[51] Int. Cl.$^4$ .............................................. G01J 3/50
[52] U.S. Cl. .................... 356/406; 356/407; 356/420
[58] Field of Search ............... 356/402, 406, 407, 409, 356/414, 416, 419, 420, 425; 250/226

[56] References Cited

U.S. PATENT DOCUMENTS

| | | | |
|---|---|---|---|
| 3,910,701 | 10/1975 | Henderson et al. ................. | 250/226 |
| 4,180,330 | 5/1979 | Kotera et al. ......................... | 356/425 |
| 4,603,976 | 8/1986 | Fetzer et al. ......................... | 356/402 |

FOREIGN PATENT DOCUMENTS

| | | |
|---|---|---|
| 99439 | 8/1973 | Fed. Rep. of Germany . |
| 2710722 | 9/1978 | Fed. Rep. of Germany . |
| 3418839 | 11/1985 | Fed. Rep. of Germany ...... 356/414 |
| 2477705 | 9/1981 | France ................................ 356/402 |
| 0123986 | 10/1978 | Japan .................................... 356/402 |

Primary Examiner—F. L. Evans
Attorney, Agent, or Firm—Andrew R. Basile; William M. Hanlon, Jr.

[57] ABSTRACT

An apparatus for rapid colorimetry on different samples which has a transmitter for irradiating or through-radiating the particular sample and a receiver for receiving the radiation reflected or transmitted by the sample, as well as a filter arrangement. Also included is a computer for evaluating the signals from the receiver. The transmitter is formed by several semiconductor radiation sources, which irradiate in different spectral ranges and whose optical radiation is combined by means of a filter unit and is deflected onto the sample by a lens arrangement. A control unit controls the semiconductor radiation sources in successive pulsewise intervals. The control unit also supplies a signal permitting an association of the receiver signals to the radiation emitted in the different spectral ranges.

7 Claims, 3 Drawing Sheets

APPARATUS FOR RAPID COLORIMETRY ON DIFFERENT SAMPLES

BACKGROUND OF THE INVENTION

1. Field of the Invention:

The present invention relates to an apparatus for rapid colorimetry on different samples.

II. Brief Description of the Relevant Art:

To an increasing extent, manufacturing processes are being automated and monitored so that additional information in the form of bar codes, colored dots, colored rings and the like are impressed on the products to be worked. The products thus marked carry significant data in coded form which determine the production sequence and the marketing routing. Such marks must be detected by means of a scanner. Monochromatic bar codes are detected in known manner by light barriers or reflection scanners, in which a semiconductor diode or miniature bulb illuminates the object and a photodiode detects the reflected or transmitted radiation. Such known scanners are not suitable for detecting polychromatic marks and for distinguishing the colors thereof.

The relevant art discloses a color detection system in which halogen lamps are used as light sources and produce a white constant light radiation or emission, which is used for irradiating the object to be measured. The colorimetric values are obtained by means of several photoreceivers or photodetectors, upstream of each of which are connected color filters with different transmission ranges. These values are supplied to a computer, which effects the evaluation and associated of the signal supplied by the receiver with respect to the individual colors. In this known arrangement, the measuring field illumination, i.e. of the transmitter, is relatively large and, as a result of the halogen lamps, produces undesired heat. In addition, protection against parasitic light is necessary, because such light would otherwise also be detected by the photoreceivers. In addition, the measuring time of approximately 8 milliseconds is relatively long.

SUMMARY OF THE INVENTION

The object of the present invention is to provide an apparatus for rapid colorimetry on different samples which is suitable for detecting different colors, has a rapid reading speed, while also being compact and maintenance-free.

The apparatus of the present invention is capable of performing rapid colorimetry on different samples and has a transmitter for irradiating or through-radiating the particular sample. The device also has a receiver for receiving the reflected or transmitted radiation from the sample.

The transmitter according to the invention has several semiconductor radiation sources, preferably three luminescent or light-emitting diodes in the blue, green and red spectral range, whose optical radiation is combined by means of a filter unit and is deflected by a lens unit to the sample. There is also a control unit, which controls the individual semiconductor radiation sources in successive pulses. Also included is a photoelectric receiver which receives the reflected or transmitted radiation. A signal supplied by the control unit permits association of the receiver signals with the radiation emitted in the different spectral ranges. As a result of this inventive arrangement, extremely rapid color detection can be obtained. The measuring cycle for all three colors can be less than 100 microseconds. The optical resolution is very high, so that small marks or symbols can also be detected. As a result of the use of semiconductor light sources, the inventive arrangement can be constructed in a very compact and maintenance-free manner in which parasitic light does not significantly impair the measurements.

It is particularly advantageous to use dichroic mirrows or reflectors. These dichroic mirrors function as separation filters. Preferably a blue mirror and a red mirror are employed so that it is possible to simply combine the radiations of the different semiconductor radiation sources on one lens arrangement. Through the arrangement of the mirrors at an angle of about 45° to the semiconductor radiation sources, a deflection of red and blue radiation is ensured, while the green radiation is allowed to pass through the mirrors.

According to an advantageous development, the excitation capacity in the case of pulsed control of the individual semiconductor radiation sources can be separately predetermined, so that the individual radiation sources can be calibrated in such a way that they bring about measured values defined on a standard on the radiation receiver.

Due to the fact that the transmitter and receiver are housed in one casing and their association in the casing is brought about in such a way that the receiver is at an angle of about 45° to the radiation emitted by the transmitter, a color-normal scanning head is made available, which is particularly small and maintance-free.

BRIEF DESCRIPTION OF THE DRAWINGS

The invention is described in greater detail hereinafter relative to a non-limitative embodiment and the attached drawings,m in which.

DETAILED DESCRIPTION OF THE INVENTION

Figure 3:
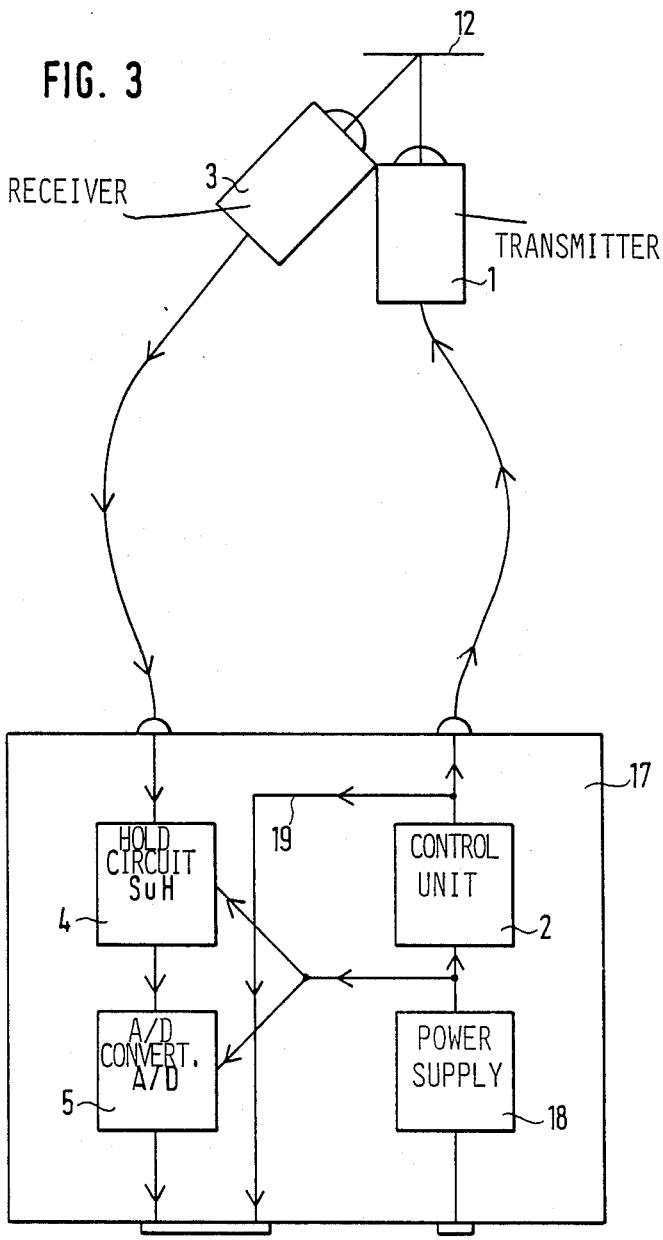
FIG. 3 is a block circuit diagram of the evaluation and control unit.

As shown, particularly, in the schematic diagram in FIG. 3, the apparatus for the rapid colorimetry of different samples comprises a transmitter 1, which is connected to a control unit 2, a receiver 3 with downstream-connected evaluation unit 4, 5 and a computer connected to the evaluation unit.

Figure 1:
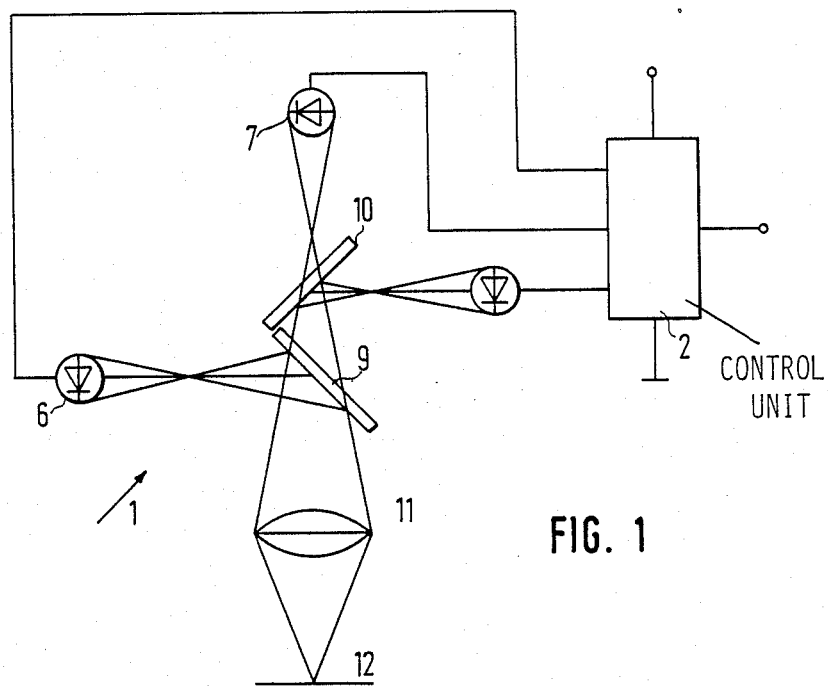
FIG. 1 shows a schematic view of the basic arrangement of the semiconductor radiation sources of the filter unit and the lens arrangement of the transmitter.
Figure 5:
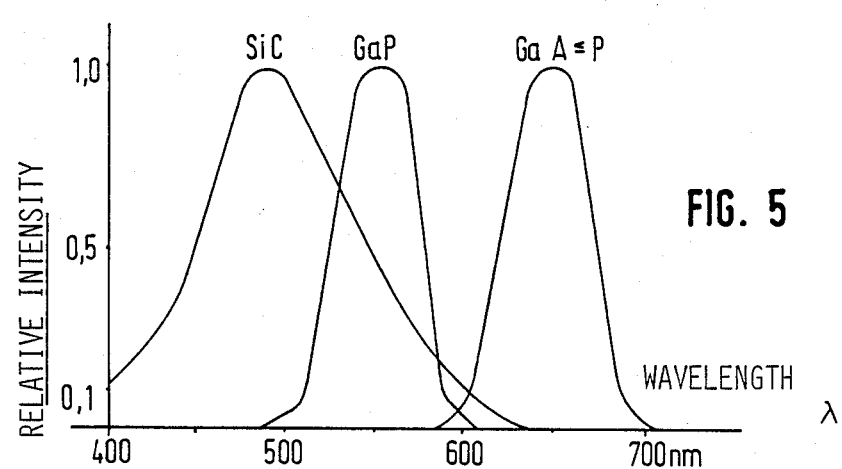
FIG. 5 is a graphic representation of the position of the emission spectra of the light-emiting diodes used in an embodiment.

Transmitter 1 as shown in FIG. 1 has three light-emitting diodes 6, 7, 8. Diode 6 irradiates in the blue spectral range, diode 7 in the green spectral range, and diode 8 in the red range. The position of the emission spectra of the diodes 6, 7, 8 is shown in FIG. 5. It can be seen that the maxima of the emitted radiations occur at approximately 480 nm (blue), 555 nm (green) and 670 nm (red). In the optical path of light-emitting diodes 6, 7, 8 are connected color separating filters which form two dichroic mirrors 9, 10, which are at an angle of 45° to the irradiation direction of the blue and red diodes 6, 8, so that the blue radiation of diode 6 is deflected on the "blue mirror" 9 and the red radiation of diode 8 is deflected on the "red mirror" 10, while passing through the "blue mirror" 9. The green radiation from light-emitting diode 7 passes both through the "red mirror" 10 and the "blue mirror" 9, so that the radiations of the individual diodes are combined to form a single radiation, which is deflected through a lens arrangement 11 onto or through the sample 12 to be measured. The individual optical elements, i.e. the light-emitting diodes 6, 7, 8, the dichroic mirrors 9, 10 and the lens arrangement 11, are adjusted in such a way that the individual beams meet at one point, wher the sample 12 must be located.

Figure 4:
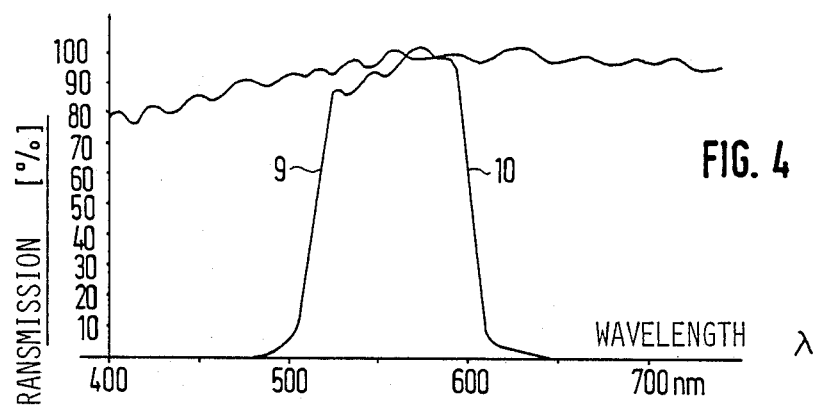
FIG. 4 is a graphic representation of the transmission characteristics of the dichroic mirrors.

The transmission curves of the dichroic mirrors are shown in FIG. 4. It can be seen that the "blue mirror" 9 transmits the radiation at a wavelength of approximately 510 nm, i.e. the radiation is reflected in the blue range. The same applies for the "red mirror" 10, which transmits radiation up to approximately 610 nm and blocks the red range. This means that the "blue mirror" 9 permits the passage of both the green and he red radiation, whereas the "red mirror" 10 permits the passage of the green and blue radiation.

It is to be understood that the combination of the radiations of the three light-emitting diodes 6, 7, 8 can also take place in other ways within the preview of this invention, e.g. by means of beam splitting plates and price cubes. However, the above-described arrangement constitutes the preferred embodiment.

Figure 2:
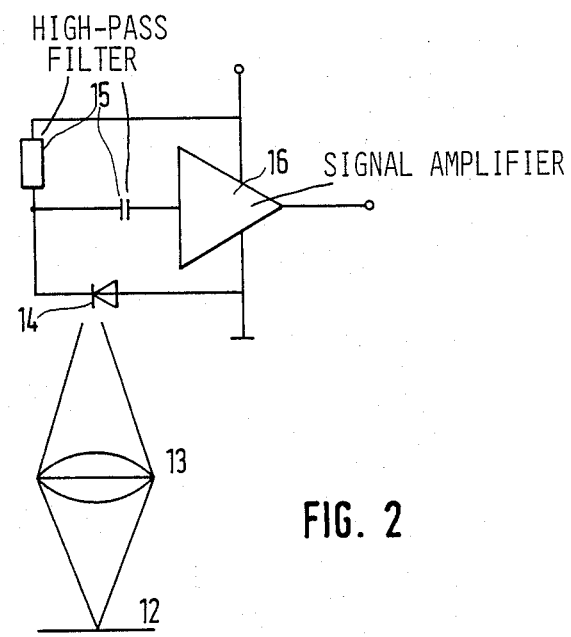
FIG. 2 is a wiring diagram of the receiver.

The present invention also includes a receiver 3 as shown in FIG. 2. The receiver 3 has a receiver optic 13, which collects light reflected or transmitted by sample 12 and brings it to the actual photoreceiver 14. In the preferred embodiment, the photoreceiver 14 can be constructed as a photodiode. Photoreceiver 14 is selected in such a way that it has a short response time and a high quantum yield. Photoreceiver 14 is connected to a signal amplifier 16 wired with a high-pass filter 15 and which suppresses low frequency parasitic light scattering, e.g. from fluorescent lamps.

The control and evaluation unit 17 as shown in FIG. 3 includes a power supply 18. Control unit 2 controls transmitter 1 pulsewise, i.e. each light-emitting diode successively receives an excited, fixed, timed pulse with three pulses determining a cycle. In each cycle each diode 6, 7, 8 responds once and on each occasion emits one light pulse. The control logic has a clock timing or mechanism for this purpose.

In addition, control logic 2 emits a synchronizing signal, which is available at the output of the control and evaluation unit via line 19. The high frequency radiation pulses reflected or transmitted by the sample are detected by receiver 3 and converted into electrical pulses, which are supplied to the evaluation unit, which has a sample and hold circuit 4 to store the pulses from the signal amplifier 16 for the duration of a cycle. Downstream of the sample and the hold circuit 4 is connected an A/D converter 5, which converts the colorimetry values corresponding to the different voltages into digital values, e.g. into 8 bit values. These digital values are available at the output of the control and evaluation unit and are supplied to a computer (not shown). which, with the aid of the synchronizing signals, effects an association of the measured values and further processes them.

As the efficiency of the light-emitting diodes 6, 7, 8 varies and also diodes of the same special ranges have tolorances, the control unit 2 is constructed in such a way that the excitation capacity can be separately predetermined on the individual diodes 6, 7, 8. The excitation capacity can be defined as the duration and level of the control pulses. For example, the excitation capacity of the particular light-emitting diodes 6, 7, 8 is adjusted in such a way that, when using a standard such as a white standard of barium sulphate, clearly defined output voltages of approximately 2 volts are present at receiver 3 during the reflection measurement.

In each case, one light pulse of each light-emitting diode 6, 7, 8 is required for the measurement of a sample, so that the single serial switching on of all the diodes constitutes a measuring cycle and the minimum measuring time corresponds to the cycle time. In the present invention this measuring cycle amounts cycle amounts to an interval greater than or equal to 100 microseconds so that very rapid measurements can be performed.

Figure 6:
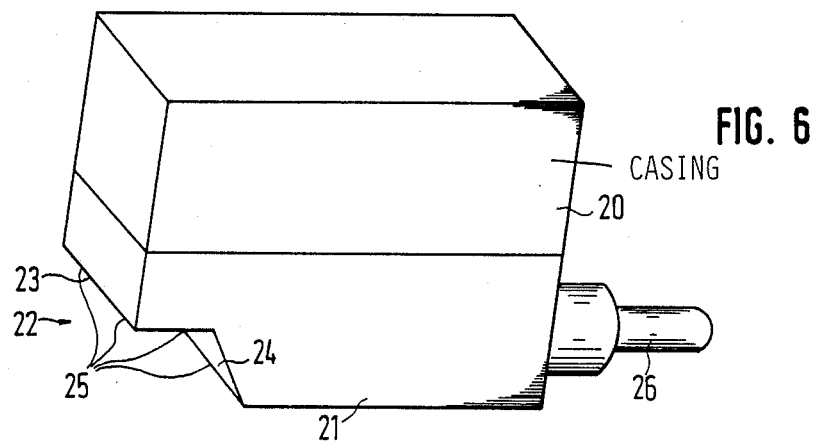
FIG. 6 is a perspective view of the colorimetry head according to the present invention.

A suitable colorimetry head used in the invention apparatus is shown in FIG. 6. The colorimetry head includes casing 20 which contains transmitter 1, receiver 3 and the control and evaluation unit 17. A connecting line 26 leads to a computer (not shown). This colorimetry head is to be used for reflectance measurements while transmission measurements can also be performed if a mirror is positioned behind the transparent sample. The base surface 21 of casing 20 is provided with a step 22, so that there is a surface 23 parallel to base surface 21 and a sloping surface 24 is formed, which connects surface 23 to base surface 21. Surfaces 23, 24 contain the passage openings to the transmitter and receiver or the lens arrangement 11, 13 for the transmitter and receiver. The sloping surface 24 preferably has an angle such that the reflectance measurement can be performed under 45°. The distance between the base surface 21 of the colorimetry head and the substrate on which the sample 12 is located must be selected in such a way that the illuminating spot 25 is as small as possible and preferably has a diameter of approximately 1mm. This spacing can be filled by adjusting disks (not shown), which are placed under the base surface 21.

What is claimed is:
1. An apparatus for rapid colorimetry on different samples comprising:
   (a) a transmitter capable of irradiating or through-radiating the particular sample;
   (b) three semiconductor radiation sources located in the transmitter which irradiate in the red, green and blue spectral ranges, respectively;
   (c) a unitary photoelectric receiver capable of receiving the radiation reflected or transmitted by the sample and generating signals;
   (d) a filter unit arrangement capable of combining optical radiation emitted from the semiconductors associated with the transmitter by means of two dichroic mirrors, each located at an angle of 45 degrees to the direction of the radiation emitted by one of the semiconductor radiation sources;
   (e) a computer capable of evaluating the signal supplied by the receiver;
   (f) a lens arrangement associated with the transmitter capable of focusing the combined optical radiation from the filter unit arrangement onto the particular sample;

(g) a control unit capable of providing successive pulses to control the semiconductor radiation sources, the control unit also capable of generating a signal permitting an association of the receiver signals with the radiation emitted in the different spectral ranges; and (h) the semiconductor radiation sources, the filter unit and the lens arrangement adjusted in such a way that all the individual beams meet at one point forming an illuminating spot, the diameter of the illuminating spot being adaptable to the particular sample.

2. The apparatus according to claim 1, wherein the illuminating spot has a diameter of approximately 1 mm.

3. The apparatus according to claim 1, wherein the transmitter and receiver are placed in one casing, the receiver being at an angle of 45° to the radiation directed onto the sample.

4. the apparatus according to claim 1, wherein exciting capacities for the individual semiconductor radiation sources of the transmitter can be separately predetermined.

5. The apparatus according to claim 1, wherein for one measuring cycle of the sample, each semiconductor radiation source is controlled at least once by one pulse.

6. An apparatus according to claim 1, wherein at least one of the dichroic mirrors reflects in the red spectral range and at least one dichroic mirror reflects in the blue spectral range.

7. The apparatus according to claim 1, wherein the semiconductor radiation sources are constructed as three light-emitting diodes which emit radiation in the red, green and blue spectral ranges respectively and the filter unit has at least two dichroic mirrors located at an angle of approximately 45° to the respective directions of radiation emitted by the individual semiconductor radiation sources, wherein at least one dichroic mirror reflects light in the red spectral range and at least one other dichroic mirror reflecting light in the blue range.

* * * * *